(12) United States Patent
Chavarria et al.

(10) Patent No.: US 11,771,560 B2
(45) Date of Patent: *Oct. 3, 2023

(54) MODULAR REVERSE SHOULDER ORTHOPAEDIC IMPLANT AND METHOD OF IMPLANTING THE SAME

(71) Applicant: DEPUY SYNTHES PRODUCTS, INC., Raynham, MA (US)

(72) Inventors: Jason M. Chavarria, Warsaw, IN (US); Dwight T. Todd, Fort Wayne, IN (US); Didier Poncet, Villeurbanne (FR)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/504,868

(22) Filed: Oct. 19, 2021

(65) Prior Publication Data

US 2022/0039962 A1 Feb. 10, 2022

Related U.S. Application Data

(60) Continuation of application No. 16/393,294, filed on Apr. 24, 2019, now Pat. No. 11,147,678, which is a
(Continued)

(51) Int. Cl.
*A61F 2/40* (2006.01)
*A61F 2/30* (2006.01)
*A61B 17/84* (2006.01)

(52) U.S. Cl.
CPC .......... *A61F 2/4014* (2013.01); *A61F 2/4059* (2013.01); *A61B 17/842* (2013.01);
(Continued)

(58) Field of Classification Search
CPC ............ A61F 2/4014; A61F 2002/3615; A61F 2002/4011; A61F 2002/4018;
(Continued)

(56) References Cited

U.S. PATENT DOCUMENTS 5,489,310 A 2/1996 Mikhail
5,769,856 A 6/1998 Dong et al.
(Continued)

FOREIGN PATENT DOCUMENTS

EP 329854 A1 8/1989
EP 1402854 A2 3/2004
(Continued)

OTHER PUBLICATIONS

Japanese Office Action with English translation for Japanese Application No. 2016-005043, dated Nov. 12, 2019, 11 pages.
(Continued)

*Primary Examiner* — Megan Y Wolf
(74) *Attorney, Agent, or Firm* — BARNES & THORNBURG LLP

(57) ABSTRACT

A modular reverse shoulder orthopaedic implant includes a humeral stem component and a separable fracture epiphysis component having a number of suture holes formed therein. The fracture epiphysis component is configured to receive a number of sutures for surgically repairing a proximal humeral fracture.

7 Claims, 16 Drawing Sheets

Related U.S. Application Data continuation of application No. 15/465,233, filed on Mar. 21, 2017, now Pat. No. 10,368,998, which is a division of application No. 14/597,662, filed on Jan. 15, 2015, now Pat. No. 9,597,190.

(52) U.S. Cl.
CPC .............. *A61F 2002/3082* (2013.01); *A61F 2002/30331* (2013.01); *A61F 2002/30433* (2013.01); *A61F 2002/30461* (2013.01); *A61F 2002/30507* (2013.01); *A61F 2002/30604* (2013.01); *A61F 2002/30884* (2013.01); *A61F 2002/4022* (2013.01); *A61F 2002/4037* (2013.01); *A61F 2002/4044* (2013.01); *A61F 2002/4074* (2013.01)

(58) Field of Classification Search
CPC ...... A61F 2002/4022; A61F 2002/4029; A61F 2002/4033; A61F 2002/4059; A61F 2002/4062; A61F 2002/4066
See application file for complete search history.

(56) References Cited

U.S. PATENT DOCUMENTS

| | | | |
|---|---|---|---|
| 6,165,224 | A | 12/2000 | Alain |
| 6,334,874 | B1 | 1/2002 | Tornier et al. |
| 6,398,812 | B1 | 6/2002 | Masini |
| 6,530,957 | B1 | 3/2003 | Jack |
| 6,790,234 | B1 | 9/2004 | Frankle |
| 6,899,736 | B1 | 5/2005 | Rauscher et al. |
| 7,070,622 | B1 | 7/2006 | Brown et al. |
| 7,175,663 | B1 | 2/2007 | Stone |
| 7,241,314 | B1 | 7/2007 | Winslow |
| 7,462,197 | B2 | 12/2008 | Fornier et al. |
| 7,556,652 | B2 | 7/2009 | Angibaud et al. |
| 7,621,961 | B2 | 11/2009 | Stone |
| 7,854,768 | B2 | 12/2010 | Wiley et al. |
| 8,062,376 | B2 | 11/2011 | Shultz et al. |
| 8,070,820 | B2 | 12/2011 | Winslow et al. |
| 8,080,063 | B2 | 12/2011 | Ferrand et al. |
| 8,118,875 | B2 | 2/2012 | Rollet |
| 8,337,563 | B2 | 12/2012 | Roche et al. |
| 8,500,815 | B2 | 8/2013 | Fockens |
| 8,512,410 | B2 | 8/2013 | Metcalfe et al. |
| 8,591,591 | B2 | 11/2013 | Winslow et al. |
| 8,632,597 | B2 | 1/2014 | Lappin |
| 8,632,598 | B2 | 1/2014 | McDaniel et al. |
| 8,840,672 | B2 | 9/2014 | Winslow et al. |
| 8,845,743 | B2 | 9/2014 | Termanini |
| 8,870,962 | B2 | 10/2014 | Roche et al. |
| 8,940,054 | B2 | 1/2015 | Wiley et al. |
| 9,044,330 | B2 | 6/2015 | Chavarria et al. |
| 9,597,190 | B2 | 3/2017 | Chavarria et al. |
| 11,147,678 | B2 * | 10/2021 | Chavarria ............ A61F 2/4059 |
| 2004/0064187 | A1 | 4/2004 | Ball et al. |
| 2005/0177241 | A1 | 8/2005 | Angibaud et al. |
| 2007/0156246 | A1 | 7/2007 | Meswania et al. |
| 2007/0173945 | A1 | 7/2007 | Wiley et al. |
| 2007/0225818 | A1 | 9/2007 | Reubelt et al. |
| 2008/0177393 | A1 | 7/2008 | Grant et al. |
| 2008/0208348 | A1 | 8/2008 | Fitz |
| 2009/0171462 | A1 | 7/2009 | Poncet et al. |
| 2009/0210065 | A1 | 8/2009 | Nerot et al. |
| 2009/0306782 | A1 | 12/2009 | Schwyzer |
| 2011/0060417 | A1 | 3/2011 | Simmen et al. |
| 2011/0106266 | A1 | 5/2011 | Schwyzer et al. |
| 2011/0130840 | A1 | 6/2011 | Oskouei |
| 2012/0029647 | A1 | 2/2012 | Winslow et al. |
| 2012/0101583 | A1 | 4/2012 | Lascar et al. |
| 2012/0179262 | A1 | 7/2012 | Metcalfe et al. |
| 2012/0253467 | A1 | 10/2012 | Frankle |
| 2012/0330428 | A1 | 12/2012 | Splieth et al. |
| 2013/0150973 | A1 | 6/2013 | Splieth et al. |
| 2013/0197652 | A1 | 8/2013 | Ekelund et al. |
| 2013/0289738 | A1 | 10/2013 | Humphrey |
| 2014/0039633 | A1 | 2/2014 | Roche et al. |
| 2014/0128981 | A1 | 5/2014 | Lappin |
| 2014/0156011 | A1 | 6/2014 | Termanini |
| 2014/0188232 | A1 | 7/2014 | Metcalfe et al. |
| 2014/0236304 | A1 | 8/2014 | Hodorek et al. |
| 2014/0243986 | A1 | 8/2014 | Frankle |
| 2014/0364953 | A1 | 12/2014 | Tomlinson et al. |
| 2015/0012103 | A1 | 1/2015 | Winslow et al. |
| 2015/0088262 | A1 | 3/2015 | Lappin |
| 2015/0127110 | A1 | 5/2015 | Lappin |
| 2017/0189196 | A1 | 7/2017 | Chavarria et al. |

FOREIGN PATENT DOCUMENTS

| | | |
|---|---|---|
| EP | 1804729 A2 | 7/2007 |
| EP | 1937188 A2 | 7/2008 |
| EP | 1996125 A2 | 12/2008 |
| EP | 2001414 A2 | 12/2008 |
| EP | 2124829 A2 | 12/2009 |
| EP | 2242452 A1 | 10/2010 |
| EP | 2301481 A1 | 3/2011 |
| EP | 2405866 A1 | 1/2012 |
| EP | 2474288 A1 | 7/2012 |
| EP | 2604227 A1 | 6/2013 |
| EP | 2665445 A1 | 11/2013 |
| EP | 2668930 A1 | 12/2013 |
| EP | 2672929 A2 | 12/2013 |
| EP | 2773290 A1 | 9/2014 |
| EP | 2779951 A1 | 9/2014 |
| EP | 2841021 A1 | 3/2015 |
| EP | 2844194 A1 | 3/2015 |
| EP | 2854712 A1 | 4/2015 |
| FR | 2972627 A1 | 9/2012 |
| JP | 2007503861 A | 3/2007 |
| JP | 2007536944 A | 12/2007 |
| JP | 2012143562 A | 8/2012 |
| JP | 2013525047 A | 6/2013 |
| RU | 2306904 C | 9/2007 |
| RU | 138160 U1 | 3/2014 |
| WO | 2007133335 A2 | 11/2007 |
| WO | 2012051552 A2 | 4/2012 |
| WO | 2014067961 A1 | 5/2014 |
| WO | 2014096912 A1 | 6/2014 |
| WO | 2015001525 A1 | 1/2015 |
| WO | 2015048385 A1 | 4/2015 |

OTHER PUBLICATIONS

Translation of FR2972627A1 performed using Google Translate on Dec. 10, 2020 (Year: 2020).
Bell, J-E. et al., "Trends and Variation in Incidence, Surgical Treatment, and Repeat Surgery of Proximal Humeral Fractures in the Elderly," JBJS, 93A(2): 121-131, 2011.
Kim, S.H. et al., "Epidemiology of Humerus Fractures in the United States: Nationwide Emergency Department Sample, 2008," Arthritis Care Res, 64(3): 407-414, Mar. 2012.
Roux, A. et al., "Epidemiology of proximal humerus fractures managed in a trauma center," Ortho Trauma Surg Res, 98:715-719, 2012.
Palvanen, M. et al., "Update in the Epidemiology of Proximal Humeral Fractures," CORR, 442: 87-92, 2006.
Solberg, B.D. et al., "Locked Plating of 3- and 4-Part Proximal Humerus Fractures in Older Patients: The Effect of Initial Fracture Pattern on Outcome," J. Ortho Trauma, 23: 113-119, Feb. 2009.
Sproul, R.C. et al., "A systematic review of locking plate fixation of proximal humerus fractures," Injury, 42: 408-413, 2011.
Sudkamp, N. et al., "Open Reduction and Internal Fixation of Proximal Humeral Fractures with Use of the Locking Proximal Humerus Plate," JBJS, 91A: 1320-1328, 2009.
Thanasas, C. et al., "Treatment of proximal humerus fractures with locking plates: A systematic review," JSES, 18: 837-844, 2009.
Brunner, F. et al., "Open Reduction and Internal Fixation of Proximal Humerus Fractures Using a Proximal Humeral Locked Plate: A Prospective Multicenter Analysis," J. Ortho Trauma, 23: 163-172, Mar. 2009.

(56) References Cited

OTHER PUBLICATIONS

Krappinger, D. et al., "Predicting failure after surgical fixation of proximal humerus fractures," Injury, 42: 1283-1288, 2011.

Owsley, K.C. et al., "Displacement/Screw Cutout After Open Reduction and Locked Plate Fixation of Humeral Fractures," JBJS, 90A: 233-240, 2008.

Schliemann, B. et al., "Complex fractures of the proximal humerus in th elderly—outcome and complications after locking plate fixation," Musculoskeletal Surg, 96(Suppl 1): S3-S11, 2012.

Boileau, P. et al., "Tuberosity malposition and migration: Reasons for poor outcomes after hemiarthroplasty for displaced fractures of the proximal humerus," JSES, 11:401-412, 2002.

Kontakis, G. et al., "Early management of proximal humeral fractures with hemiarthroplasty," JBJS, 90B: 1407-1413, 2008.

Sirveaux, F. et al., "Reverse Prosethesis for Proximal Humerus Fracture, Technique and Results," Tech Shoulder & Elbow Surg, 9(1): 15-21, 2008.

Gallinet, D. et al., "Three or four parts complex proximal humerus fractures: Hemiarthroplasty versus reverse prosethesis: A comparative study of 40 cases," Ortho Trauma Surg Res, 95:48-55, 2009.

Green, A. et al., "Humeral head replacement for acute, four-part proximal humerus fractures," JSES, 2: 249-254, 1993.

Robinson, C.M. et al., "Primary Hemiarthroplasty for Treatment of Proximal Humeral Fractures," JBJS, 85A: 1215-1223, 2003.

Sirveaux, F. et al., "Shoulder arthroplasty for acute proximal humerus fracture," Ortho Trauma Surg Res, 96: 683-694, 2010.

Wretenberg, P. et al., "Acute hemiarthroplasty after proximal humerus fracture in old patients," Acta Ortho Scand, 68: 121-123, 1997.

Valenti, P. et al., "Mid-term outcome of reverse shoulder prostheses in complex proximal humeral fractures," Acta Ortho Belg, 78: 442-449, 2012.

Gallinet, D. et al. "Improvement in shoulder rotation in complex shoulder fractures treated by reverse shoulder arthroplasty," JSES, 22: 38-44, 2013.

Bufquin, T. et al., "Reverse shoulder arthroplasty for the treatment of three- and four-part fractures of the proximal humerus in the elderly," JBJS, 89B: 516-520, 2007.

Klein, M. et al., "Treatment of Comminuted Fractures of the Proximal Humerus in Elderly Patients With the Delta III Reverse Shoulder Prosthesis," J. Ortho Trauma, 22: 698-704, Nov./Dec. 2008.

Extended European Search Report, European Application No. 17171503.0-1664, dated Jul. 3, 2017, 9 pages.

Russian Federation Office Action and Search Report with English translation for Application No. 2015156536, dated Dec. 29, 2015, 11 pages.

* cited by examiner

MODULAR REVERSE SHOULDER ORTHOPAEDIC IMPLANT AND METHOD OF IMPLANTING THE SAME

This continuation application claims priority to U.S. patent application Ser. No. 16/393,294, now U.S. Pat. No. 11,147,678, which was filed on Apr. 24, 2019, which is a continuation of U.S. patent application Ser. No. 15/465,233, now U.S. Pat. No. 10,368,998, which was filed on Mar. 21, 2017 and which is a divisional application of U.S. patent application Ser. No. 14/597,662, now U.S. Pat. No. 9,597,190 which was filed on Jan. 15, 2015, the entirety of each of the above-identified applications is hereby expressly incorporated by reference.

TECHNICAL FIELD

The present disclosure relates generally to orthopaedic implants, and more particularly to reverse shoulder orthopaedic implants.

BACKGROUND

During the lifetime of a patient, it may be necessary to perform a total shoulder replacement procedure on the patient as a result of, for example, disease or trauma. In a total shoulder replacement procedure, a humeral prosthesis is used to replace the natural head of the patient's humerus. The humeral prosthesis typically includes an elongated stem component that is implanted into the intramedullary canal of the patient's humerus and a hemispherically-shaped prosthetic head component that is secured to the stem component. In such a total shoulder replacement procedure, the natural glenoid surface of the scapula is resurfaced or otherwise replaced with a glenoid component that provides a bearing surface upon which the prosthetic head component of the humeral prosthesis articulates.

However, in some cases the patient's natural shoulder, including its soft tissue, has degenerated to a severe degree of joint instability and pain. In many such cases, it may be necessary to change the mechanics of the shoulder. Reverse shoulder implants are used to do so. As its name suggests, a reverse shoulder implant reverses the anatomy, or structure, of the healthy shoulder. In particular, a reverse shoulder implant is designed such that the prosthetic head (i.e., the "ball" in the ball-and-socket joint) known as a glenosphere component is secured to the patient's scapula, with the corresponding concave bearing (i.e., the "socket" in the ball-and-socket joint) known as a humeral cup being secured to the patient's humerus. Such a reverse configuration allows the patient's deltoid muscle, which is one of the larger and stronger shoulder muscles, to raise the arm.

In some cases, the patient's natural shoulder anatomy has also suffered trauma such as a proximal humeral fracture. Proximal humeral fractures are one of the most common fractures among elderly patients. In a proximal humeral fracture, the patient's humerus generally breaks into a number of pieces including the humeral head, the greater tuberosity, the lessor tuberosity, and the humeral shaft.

SUMMARY

According to one aspect, a modular reverse shoulder orthopaedic implant includes an elongated humeral stem component configured to be implanted into the humerus of a patient. The implant also includes a fracture epiphysis component that is separable from the humeral stem component. The fracture epiphysis component includes a cup-shaped body having an annular rim formed in the superior end thereof. A lateral suture collar extends outwardly from the annular rim of the cup-shaped body within a segment of the annular rim defined by an anterior-most point of the rim and a posterior-most point of the rim. An anteromedial suture collar extends outwardly from the annular rim of the cup-shaped body within a segment of the annular rim defined by the anterior-most point of the rim and a medial-most point of the rim. An posteromedial suture collar extends outwardly from the annular rim of the cup-shaped body within a segment of the annular rim defined by the posterior-most point of the rim and the medial-most point of the rim. The lateral suture collar, the anteromedial suture collar, and the posteromedial suture collar are discontiguous with one another. The implant also includes a locking screw secured to the humeral stem component and the fracture epiphysis component and a humeral cup component secured to the fracture epiphysis component. The humeral cup component has a concave bearing surface configured to articulate with a rounded head surface of a glenosphere component.

Each of the lateral suture collar, the anteromedial suture collar, and the posteromedial suture collar may be embodied with a number of suture holes formed therein. In such a case, the suture holes may be positioned radially on the lateral suture collar, the anteromedial suture collar, and the posteromedial suture collar.

The lateral suture collar may be longer than both the anteromedial suture collar and the posteromedial suture collar.

In an embodiment, the anteromedial suture collar and the posteromedial suture collar are similar in size and face opposite one another along the annular rim of the cup-shaped body.

An outer surface of the cup-shaped body of the fracture epiphysis component has a plurality of suture pockets formed in a posterior end thereof. Each of such suture pockets formed in the cup-shaped body of the fracture epiphysis component is separated by a wall, with each of such walls having a suture hole formed therein.

The outer surface of the cup-shaped body of the fracture epiphysis component may also have a number of suture holes extending therethrough, with each of such suture holes extending in the anteroposterior direction.

According to another aspect, a modular reverse shoulder orthopaedic implant includes an elongated humeral stem component configured to be implanted into the humerus of a patient. The implant also includes a fracture epiphysis component that is separable from the humeral stem component. The fracture epiphysis component includes a cup-shaped body having a rounded outer surface, a channel formed in an inferior end of the rounded outer surface of the cup-shaped body, and a plurality of walls positioned in the channel so as to form a plurality of suture pockets within the channel. Each of the plurality of walls has a suture hole formed therein. The implant may also include a locking screw secured to the humeral stem component and the fracture epiphysis component and a humeral cup component secured to the fracture epiphysis component. The humeral cup component has a concave bearing surface configured to articulate with a rounded head surface of a glenosphere component.

An outer surface of the cup-shaped body of the fracture epiphysis component has an additional suture hole extending therethrough, with such an additional suture hole extending in the anteroposterior direction.

The cup-shaped body of the fracture epiphysis component may include an annular rim formed in the superior end thereof with a number of suture collars extending outwardly from the annular rim.

Each of such suture collars has a number of suture holes formed therein, with the suture holes being positioned radially on the suture collars.

The suture collars may include a lateral suture collar that extends outwardly from the annular rim of the cup-shaped body within a segment of the annular rim defined by an anterior-most point of the rim and a posterior-most point of the rim. The suture collars may also include an anteromedial suture collar extending outwardly from the annular rim of the cup-shaped body within a segment of the annular rim defined by the anterior-most point of the rim and a medial-most point of the rim. Further, the suture collars may also include an posteromedial suture collar extending outwardly from the annular rim of the cup-shaped body within a segment of the annular rim defined by the posterior-most point of the rim and the medial-most point of the rim. The lateral suture collar, the anteromedial suture collar, and the posteromedial suture collar are discontiguous with one another.

The lateral suture collar may be longer than both the anteromedial suture collar and the posteromedial suture collar.

The anteromedial suture collar and the posteromedial suture collar may be similar in size and face opposite one another along the annular rim of the cup-shaped body.

According to yet another aspect, a method of surgically repairing a proximal fracture of a patient's humerus includes rotating a locking screw to secure an elongated humeral stem component to a fracture epiphysis component and implanting the humeral stem component into the intramedullary canal of the patient's humerus. The method also includes advancing a first suture through the humeral shaft of the patient's humerus, through a first suture hole formed in an annular suture collar of the fracture epiphysis component, and through the patient's rotator cuff proximate the greater tuberosity of the patient's humerus. A second suture is advanced through the humeral shaft of the patient's humerus, through a second suture hole formed in the annular suture collar of the fracture epiphysis component, and through the patient's rotator cuff proximate the lessor tuberosity of the patient's humerus. A third suture is advanced through a third suture hole located in a suture pocket on an outer inferior surface of the of the fracture epiphysis component, through the greater tuberosity of the patient's humerus, and through the lessor tuberosity of the patient's humerus.

The method also includes tensioning the third suture so as to bring the greater tuberosity of the patient's humerus and the lessor tuberosity of the patient's humerus into contact with one another, and thereafter tying the third suture so as to secure the greater tuberosity of the patient's humerus and the lessor tuberosity of the patient's humerus in contact with one another.

The method also includes installing a polymeric humeral cup on the fracture epiphysis component subsequent to the tying step.

A tab formed in a superior surface of the humeral stem component may be positioned into one of a plurality of notches formed in an inferior surface of the fracture epiphysis component so as to position the fracture epiphysis component in a selected version angle relative the humeral stem component prior to rotation of the locking screw.

BRIEF DESCRIPTION OF THE DRAWINGS

The detailed description particularly refers to the following figures, in which.

DETAILED DESCRIPTION OF THE DRAWINGS

Figure 1:
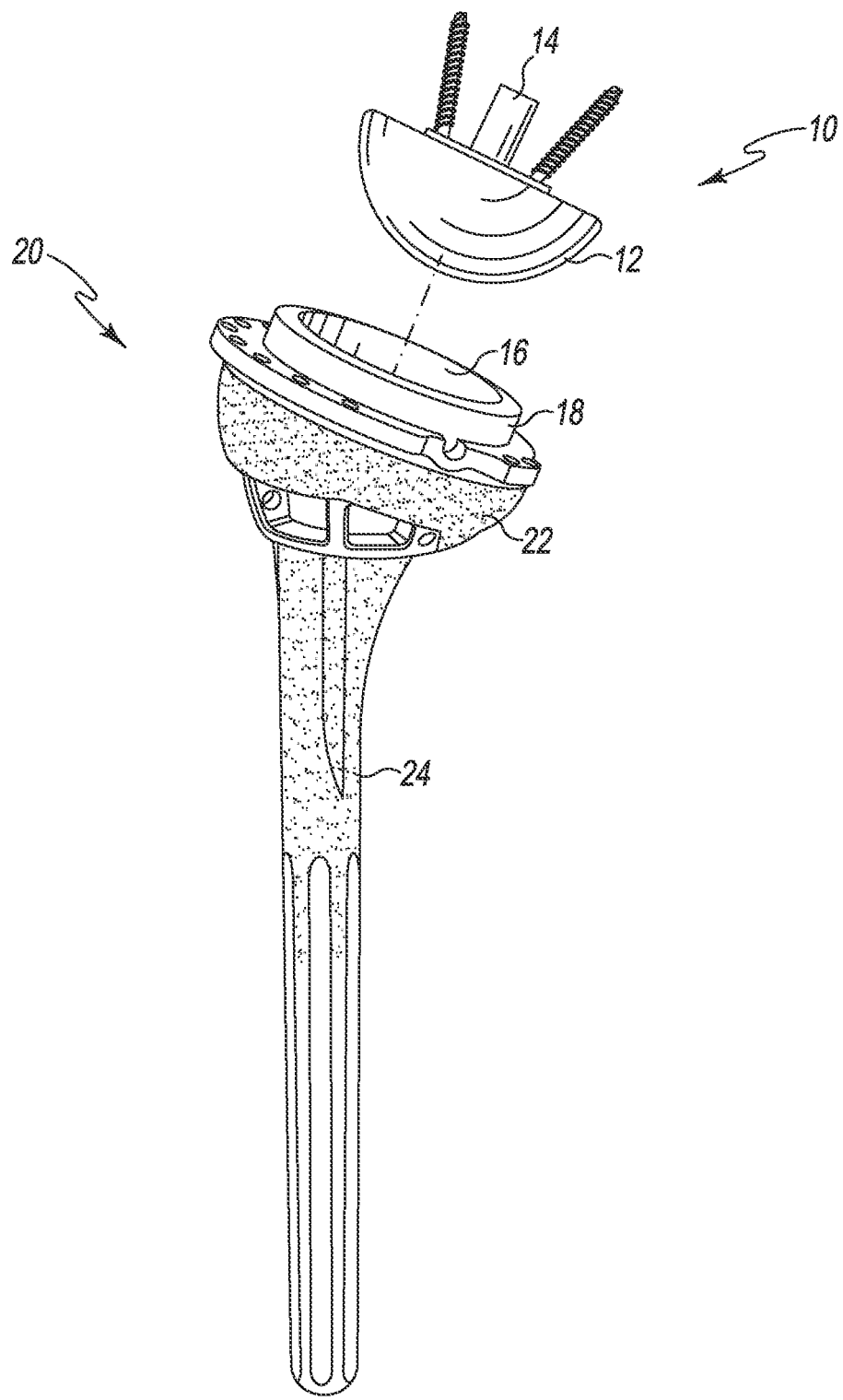
FIG. 1 is a perspective view of a modular reverse shoulder orthopaedic implant.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-5, there is shown a modular reverse shoulder orthopaedic implant 10 for replacing the natural shoulder joint of a patient subsequent to a proximal humeral fracture. The modular reverse shoulder orthopaedic implant 10 includes a rounded (e.g., hemispherically-shaped) glenosphere component 12 that is secured to the glenoid surface of the patient's scapula by a metaglene component 14 implanted in the bone tissue of the scapula. The glenosphere component 12 articulates on the bearing surface 16 of a polymeric humeral cup 18 of a modular humeral prosthesis 20. As can be seen in FIG. 1, the modular humeral prosthesis 20 includes a fracture epiphysis component 22 and a humeral stem component 24. A locking screw 26 (see FIG. 2) locks the fracture epiphysis component 22 to the humeral stem component 24 in a desired version angle (as described in more detail below). The humeral cup 18 is secured to the fracture epiphysis component 22 subsequent to implantation of the modular humeral prosthesis 20 in the intramedullary canal of a patient's humerus (see FIGS. 6-18).

Figure 5:
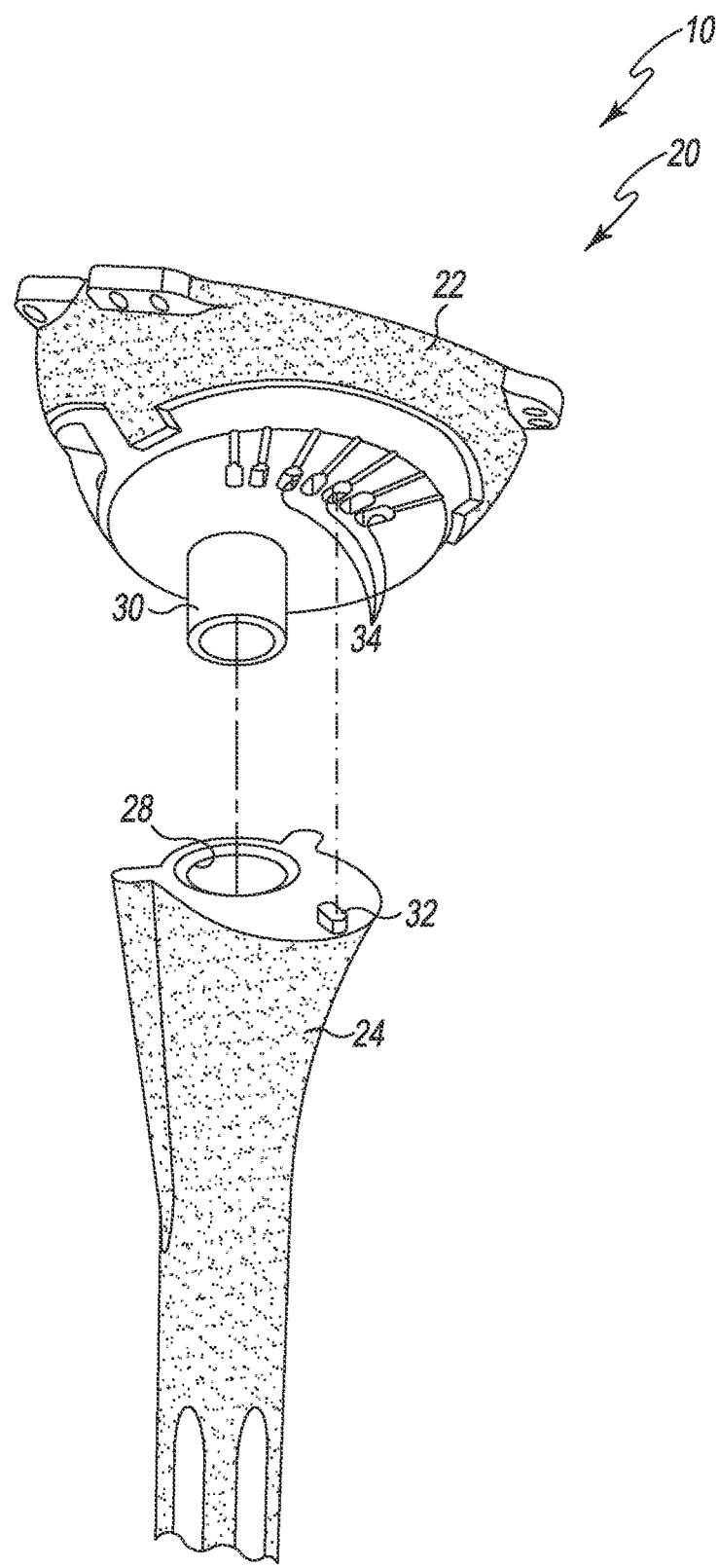
FIG. 5 is an exploded perspective view of the modular reverse shoulder orthopaedic implant of FIG. 1 showing the locking tab and locking notches for adjusting the version angle of the fracture epiphysis component relative to the humeral stem component.

As can be seen in FIG. 5, the superior end of the elongated humeral stem component 24 has a bore 28 formed therein. A cannulated post 30 formed in the inferior end of the fracture epiphysis component 22 is received into the stem component's bore 28. The sidewall defining the distal end of the stem component's bore 28 has a number of female threads defined therein (not shown). The male threads of the locking screw 26 are advanced through the cannulated post 30 of the fracture epiphysis component 22 and into threading engagement with the female threads formed in the humeral stem component 24 to lock the fracture epiphysis component 22 and the humeral stem component 24 to one another.

As can be seen in FIG. 5, the superior end of the elongated humeral stem component 24 also has a tab 32 formed therein. The tab 32 extends superiorly from the planar surface of the stem component's superior end. The planar surface of the inferior end of the fracture epiphysis component 22 has a number of notches 34 defined therein. The notches 34 are positioned radially relative to the central axis of the fracture epiphysis component's cannulated post 30. The surgeon may rotate the fracture epiphysis component 22 relative to the humeral stem component 24 such that tab 32 is received into a selected one of the notches 34 to adjust the version angle of the fracture epiphysis component 22 relative to the humeral stem component 24 prior to locking the two components to one another with the locking screw 26.

Figure 2:
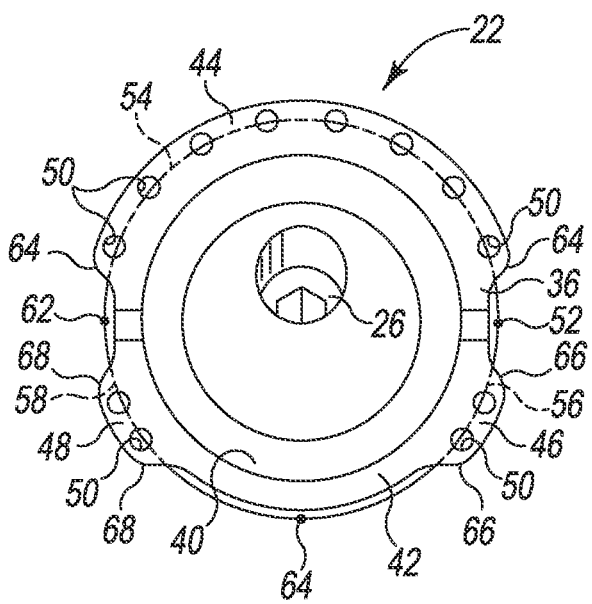
FIG. 2 is a superior elevational view of the fracture epiphysis component and the locking screw of the modular reverse shoulder orthopaedic implant of FIG. 1.
Figure 3:
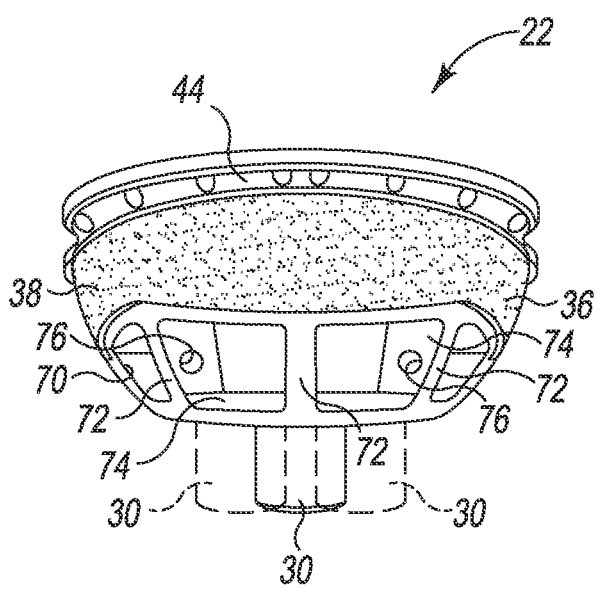
FIG. 3 is a lateral elevational view of the fracture epiphysis component of the modular reverse shoulder orthopaedic implant of FIG. 1.
Figure 4:
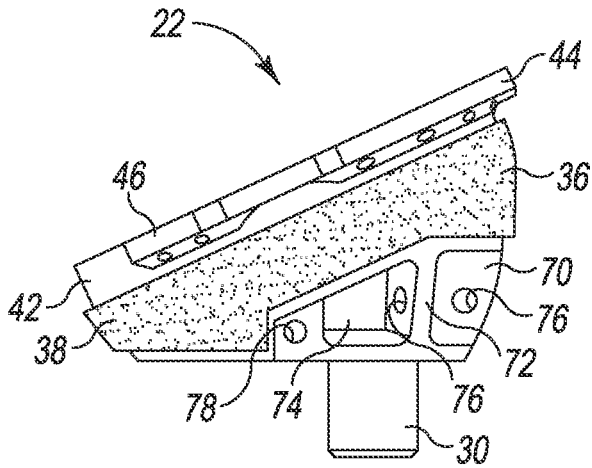
FIG. 4 is an anterior elevational view of the fracture epiphysis component of the modular reverse shoulder orthopaedic implant of FIG. 1.

As can be seen in FIGS. 2-4, the fracture epiphysis component 22 includes a cup-shaped body 36 having rounded outer surface 38. The component's body 36 has a hollow interior chamber 40 into which the humeral cup 18 is locked. The bore of the cannulated post 30 opens into the bottom of the interior chamber 40 to receive the head of the locking screw 26. The superior end of the component's body 36 defines an annular rim 42. The annular rim 42 defines the opening of the interior chamber 40.

A number of suture collars 44, 46, 48 extend outwardly from the fracture epiphysis component's annular rim 42. Specifically, in the embodiment described herein, a lateral suture collar 44 extends outwardly from a lateral segment 54 of the annular rim 42, an anteromedial suture collar 46 extends outwardly from an anteromedial segment 56 of the annular rim 42, and a posteromedial suture collar 48 extends outwardly from a posteromedial segment 58 of the annular rim 42. As can be seen in FIGS. 1-4, the suture collars 44, 46, 48 are coplanar with one another. As can be seen in FIG. 2, the lateral suture collar 44 is longer than both the anteromedial suture collar 46 and the posteromedial suture collar 48, which are both of similar size. Each of the suture collars 44, 46, 48 has a number of suture holes 50 formed therein. The suture holes 50 are positioned radially on the suture collars 44, 46, 48. As will be discussed below in more detail, sutures may be passed through the suture holes 50 to secure various features of the patient's humerus and surrounding soft tissue to the fracture epiphysis component 22 and hence the modular reverse shoulder orthopaedic implant 10.

As can also be seen in FIG. 2, the suture collars 44, 46, 48 are discontiguous with one another. In other words, the suture collars 44, 46, 48 each include distinct end edges that are spaced apart from the end edges of the other suture collars 44, 46, 48. For example, the end edges 64 of the lateral suture collar 44 are spaced apart from the respective end edges 66, 68 of both the anteromedial suture collar 46 and the posteromedial suture collar 48. Likewise, the respective end edges 66, 68 of both the anteromedial suture collar 46 and the posteromedial suture collar 48 are spaced apart from one another. This is shown geometrically in FIG. 2 in which the lateral suture collar 44 is positioned within a segment of the annular rim 42 (i.e., the lateral segment 54) defined by an anterior-most point 52 of the rim 42 and a posterior-most point 62 of the rim 42. The anteromedial suture collar 46 is positioned within a segment of the annular rim 42 (i.e., the anteromedial segment 56) defined by the anterior-most point 52 of the rim and a medial-most point 64 of the rim 42, with the posteromedial suture collar 48 being positioned within a segment of the annular rim 42 (i.e., the posteromedial segment 58) defined by the posterior-most point 62 of the rim 42 and the medial-most point 64 of the rim 42 so as to face opposite the anteromedial suture collar 46.

It should be appreciated that such an arrangement in which the suture collars 44, 46, 48 do not collectively extend all the way around the perimeter of the annular rim 42 may reduce the occurrences of impingement in some patients. In particular, depending on the anatomy of a specific patient, the design of the fracture epiphysis component 22 (i.e., it being devoid of a suture collar along its medial-most side) may reduce the occasions in which the medial side of the fracture epiphysis component would otherwise contact the scapula of the patient at certain ranges of motion. Such a configuration also facilitates mating the fracture epiphysis component 22 with an insertion tool or extraction tool during implantation or removal of the modular reverse shoulder orthopaedic implant 10.

As can be seen in FIGS. 3 and 4, the inferior end of the lateral side of the rounded outer surface 38 of the fracture epiphysis component's cup-shaped body 36 has a channel 70 formed therein. A number of walls 72 are formed in the body 36 at locations within the channel 70 thereby forming a number of suture pockets 74. Each of the walls 72 has a suture hole 76 formed therein. In a similar manner to the suture holes 50 of the suture collars suture collars 44, 46, 48, sutures may be passed through the suture holes 76 to secure various features of the patient's humerus and surrounding soft tissue to the fracture epiphysis component 22 and hence the modular reverse shoulder orthopaedic implant 10.

As can be seen in FIG. 4, one of the suture holes 76 (designated with reference numeral 78 in FIG. 4) is located on the medial side of the channel 70 and extends in the anteroposterior direction. As will be discussed below, this suture hole 78 allows for installation of an "around-the-world" or cerclage type suture.

The fracture epiphysis component 22 and the humeral stem component 24 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such metallic components 22, 24 may also be coated with a surface treatment, such as hyaluronic acid (HA), to enhance biocompatibility. Moreover, the surfaces of the fracture epiphysis component 22 and the humeral stem component 24 that engage the natural bone, such as the rounded outer surface 38 of the fracture epiphysis component 22 and the outer surfaces of the humeral stem component 24 may be textured to facilitate securing the component to the bone. Such surfaces may also be porous coated to promote bone ingrowth for permanent fixation.

Moreover, each of the components of the modular reverse shoulder orthopaedic implant 10 may be provided in various different configurations and sizes to provide the flexibility necessary to conform to varying anatomies from patient to patient. For example, the fracture epiphysis component 22 and the polymeric humeral cup 18 may be provided in various diameters to match the needs of a given patient. Moreover, as shown in phantom lines in FIG. 3, the fracture epiphysis component 22 may be provided in different configurations in which the cannulated post 30 is offset anteriorly or posteriorly (e.g., 2 mm) to provide eccentric right and left options. Further, for example, the humeral stem component 24 may be provided in various lengths and diameters to match the needs of a given patient.

Referring now to FIGS. 6-18, there is shown a surgical procedure in which the modular reverse shoulder orthopaedic implant 10 is implanted in the humerus 80 of the patient to surgically repair a proximal humeral fracture. The surgical procedure begins with preoperative planning in which, amongst other things, a CT scan or other type of preoperative image may be obtained to plan placement, location, and orientation of the modular reverse shoulder orthopaedic implant 10. With the preoperative planning complete, the patient's soft tissue is dissected and retracted in order to allow access to the fractured shoulder joint. Full exposure of the patient's shoulder joint is typically achieved.

The surgeon then assembles the modular reverse shoulder orthopaedic implant 10. Specifically, the surgeon selects a fracture epiphysis component 22 and a humeral stem component 24 of the desired size and configuration and thereafter inserts the locking screw 26 through the cannulated post 30 of the epiphysis component 22. The version angle of the fracture epiphysis component 22 relative to the humeral stem component 24 may be selected by inserting the tab 32 extending superiorly from the planar surface of the stem component's superior end into a selected one of the notches 34 formed in the inferior end of the fracture epiphysis component 22 (see FIG. 5). Thereafter, the surgeon may use a hex driver or the like (not shown) to drive the locking screw 26 thereby locking the fracture epiphysis component 22 and the humeral stem component 24 to one another. At this point in the surgical procedure, the surgeon may also assemble trial components that conform to the shape and size of the final implant for subsequent use in the procedure.

Figure 6:
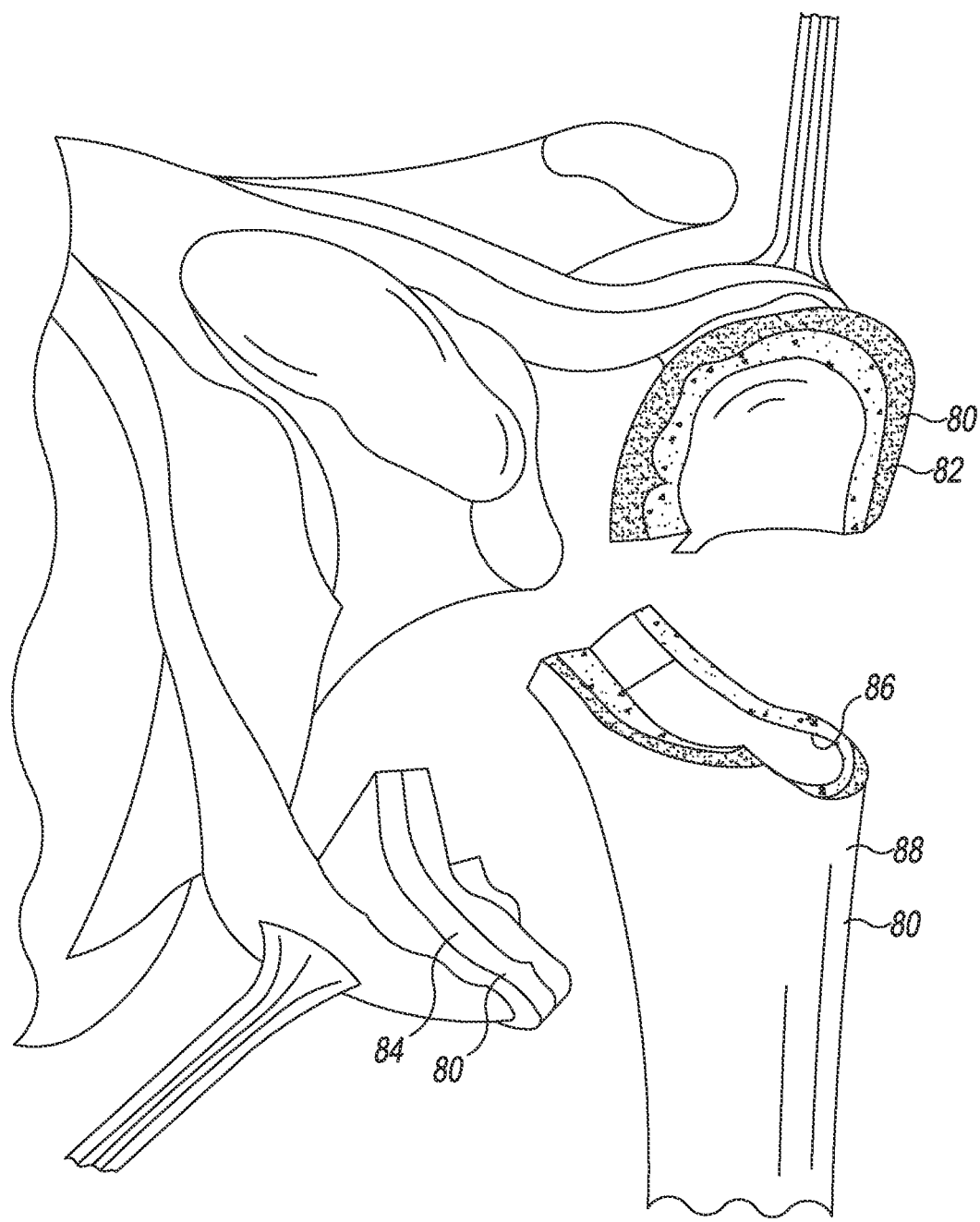
FIGS. 6-18 are perspective views showing the surgical technique for implanting the modular reverse shoulder orthopaedic implant of FIG. 1 into the humerus of a patient to surgically repair a proximal humeral fracture, note that the soft tissue (i.e., the rotator tendon) has been removed from FIGS. 17 and 18 for clarity of description.

Thereafter, as shown in FIG. 6, the patient's fractured humeral head is surgically removed and the greater tuberosity 82 and the lessor tuberosity 84 are tagged. The surgeon then prepares the intramedullary canal 86 of the patient's humerus 80 to receive the humeral stem component 24 of the reverse shoulder orthopaedic implant 10. Initially, the surgeon uses a starter reamer of a relatively small diameter and then sequentially reams with larger reamers to achieve the desired access to the patient's intramedullary canal 86. The patient's reamed humerus 80 is shown in FIG. 6.

Figure 7:
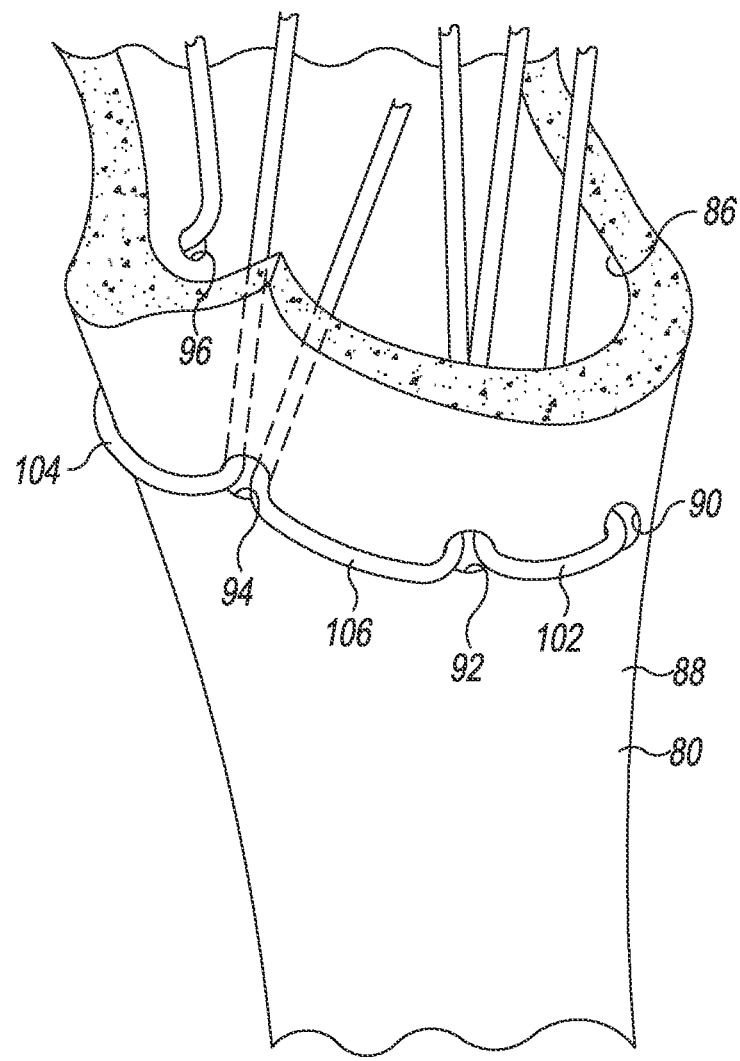

As can be seen in FIG. 7, the surgeon then drills a pair of suture holes 90, 92 through the posterolateral portion of the humeral shaft 88 at a location approximately 2 cm below the fracture line. A pair of suture holes 94, 96 are also drilled through the anterolateral portion of the humeral shaft 88 at a location approximately 2 cm below the fracture line. The surgeon then places a strand of suture 102 through the suture hole 90 in an inside to out fashion and back through the suture hole 92 thereby creating a loop outside the patient's humerus 80. As will be discussed in more detail below, this suture 102 will be utilized to re-attach the greater tuberosity 82. This process is then repeated by placing a suture 104 through suture hole 94 and suture hole 96. This suture 104 will be utilized to re-attach the lesser tuberosity 84. Another suture 106 is advanced through the suture hole 92 and the suture hole 94 thereby creating the same type of loop which will be utilized to repair the interval between the greater tuberosity 82 and lesser tuberosity 84.

Figure 8:
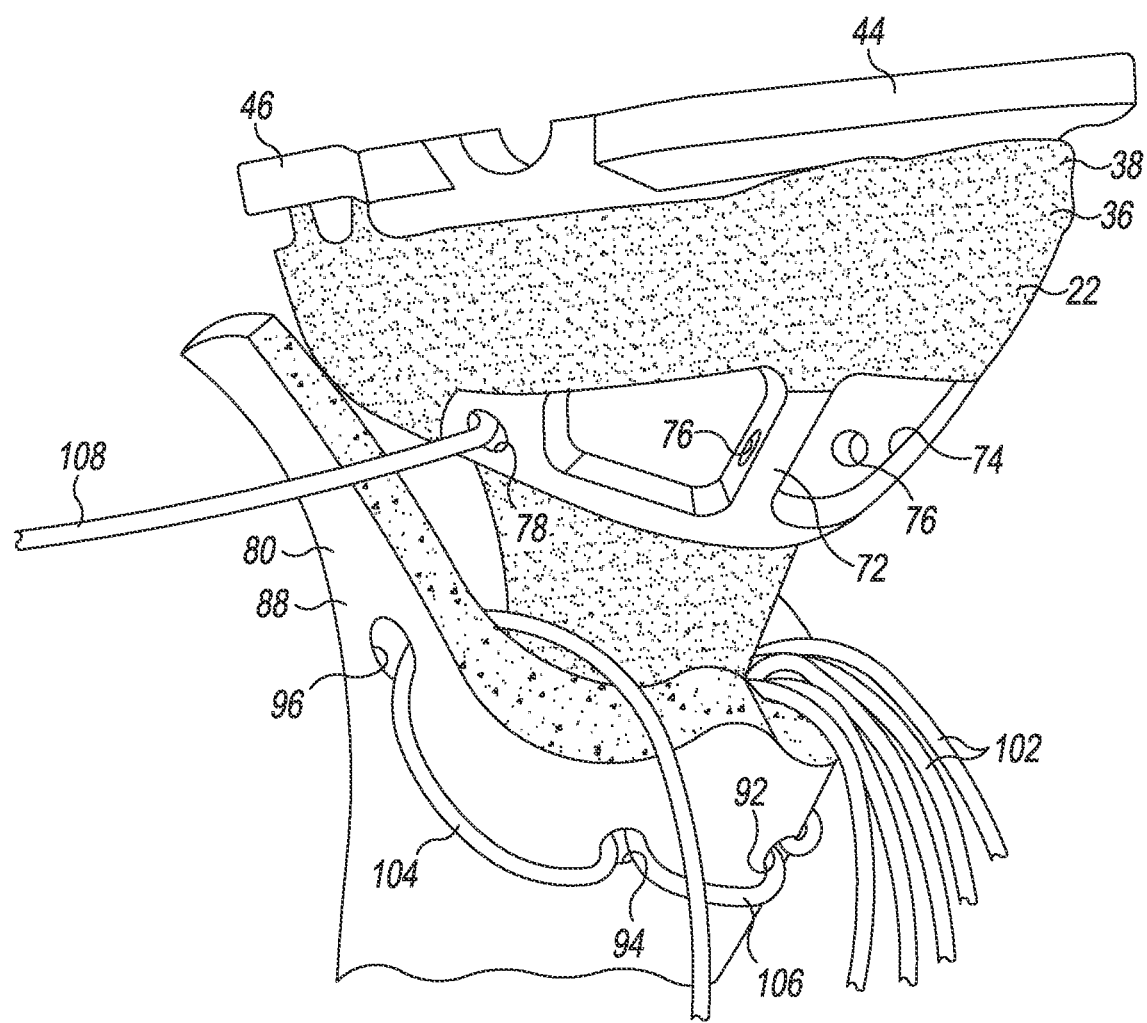

As shown in FIG. 8, an additional suture 108 is advanced through the anteroposterior suture hole 78. As will be discussed below, this suture 108 will be utilized as an "around-the-world" suture. Either before or after installation of the suture 108, the assembled and locked modular humeral prosthesis 20 (i.e., the fracture epiphysis component 22 and a humeral stem component 24) is inserted into the intramedullary canal 86 of the patient's humerus 80. A positioning jig (not shown) may be used to clamp the modular reverse shoulder orthopaedic implant 10 to the humerus 80 to set the height of the implant 10 if bone cement is used to fix the implant 10 within the intramedullary canal 86.

Figure 9:
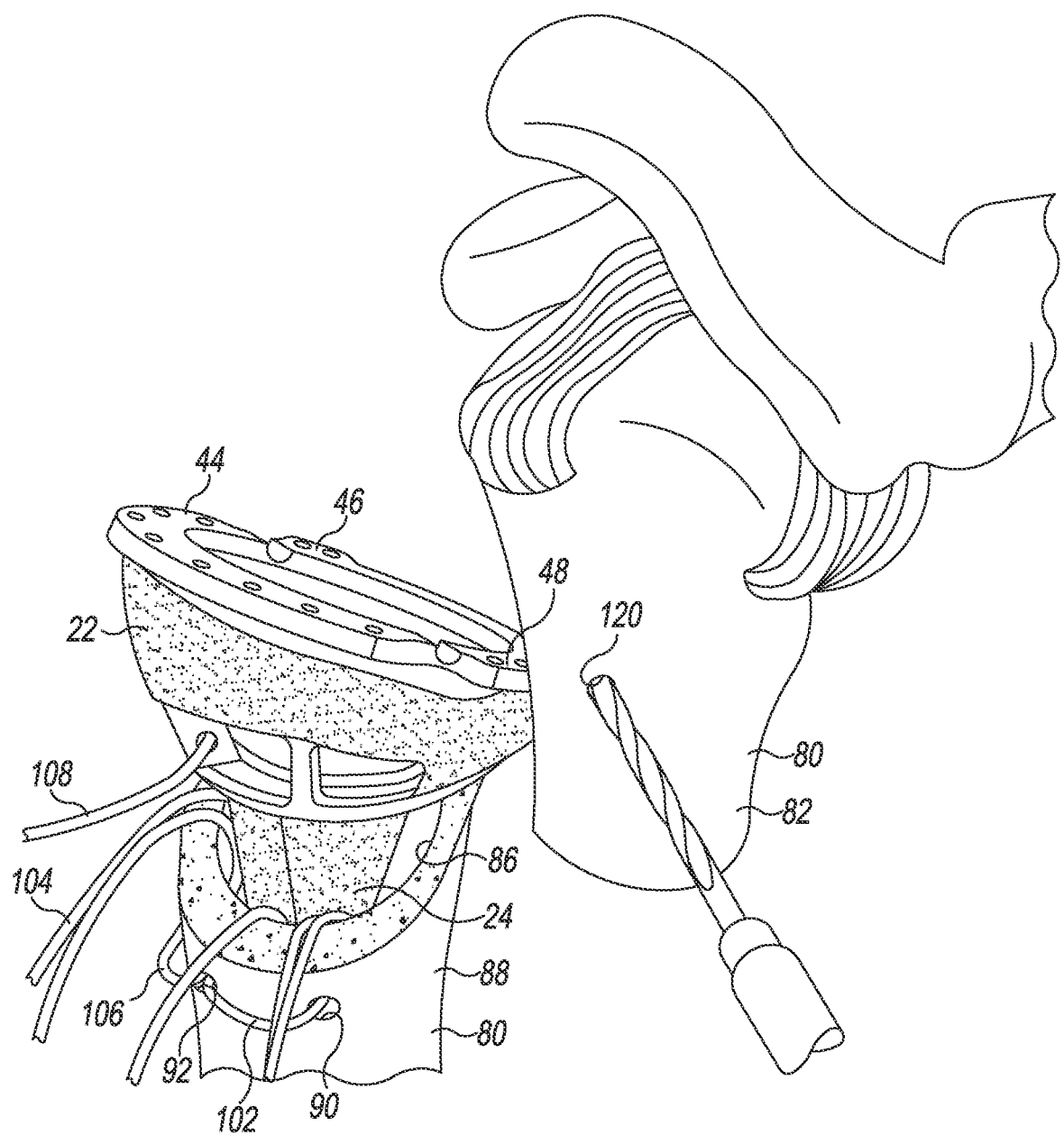
Figure 10:
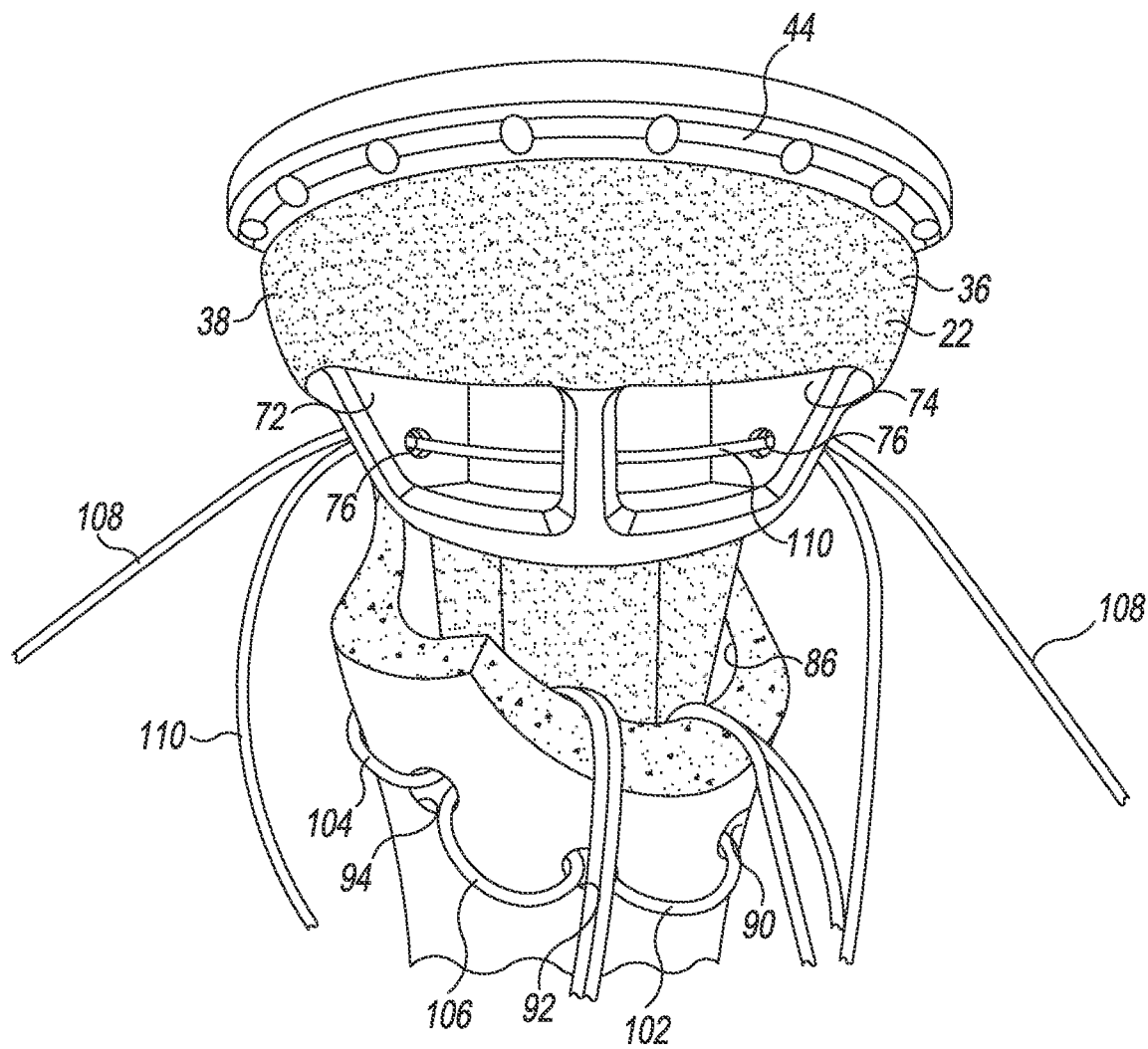

Thereafter, as shown in FIGS. 9 and 10, a hole 120 is drilled in each of the greater tuberosity 82 and the lesser tuberosity 84. As can be seen in FIG. 10, an additional suture 110 is positioned in the suture holes 76 of the fracture epiphysis component's suture pockets 74. As discussed below, this suture 110 will be passed through the drilled holes 120 to tie the tuberosities 82, 84 together with the modular reverse shoulder orthopaedic implant 10.

Figure 11:
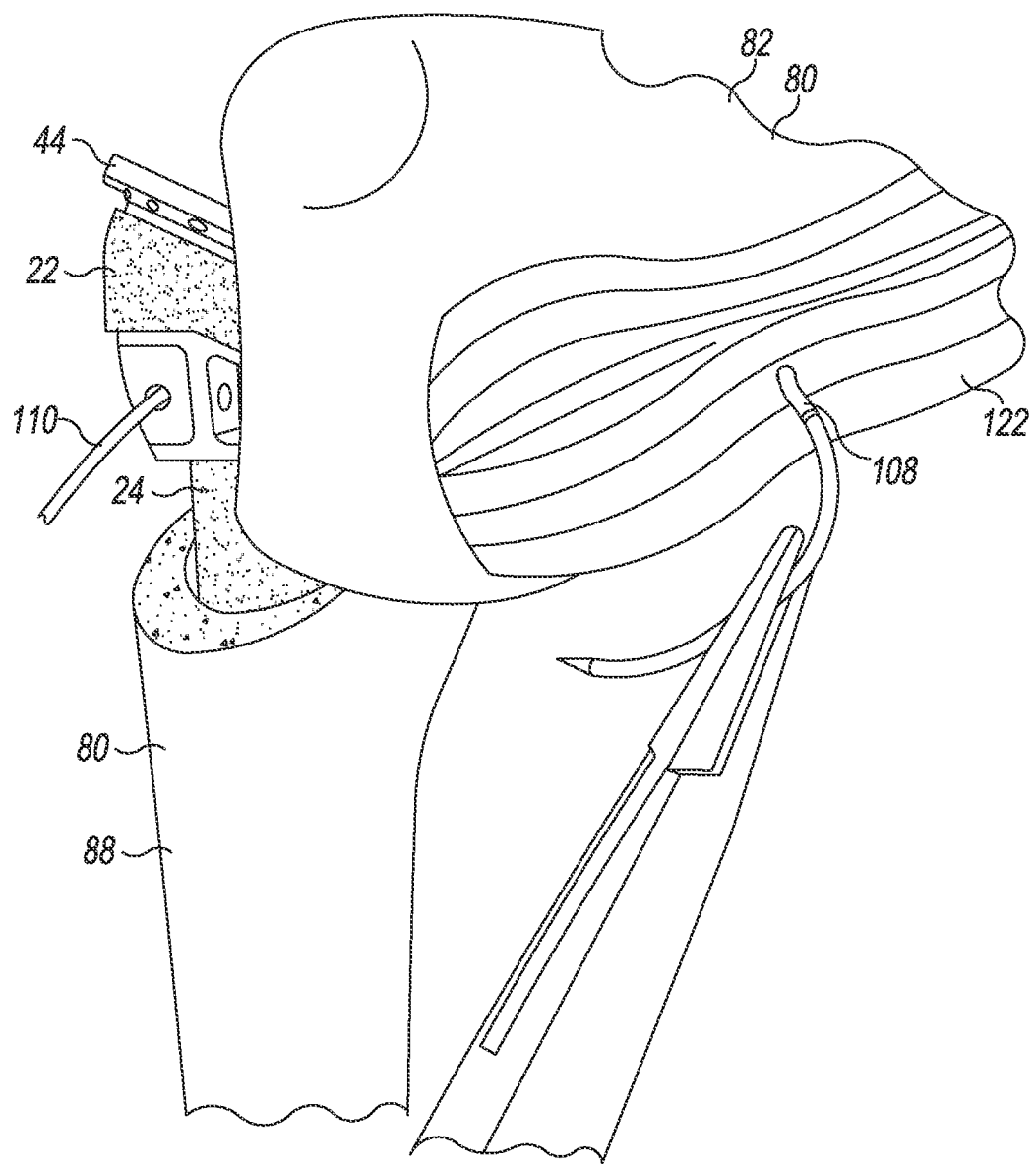
Figure 12:
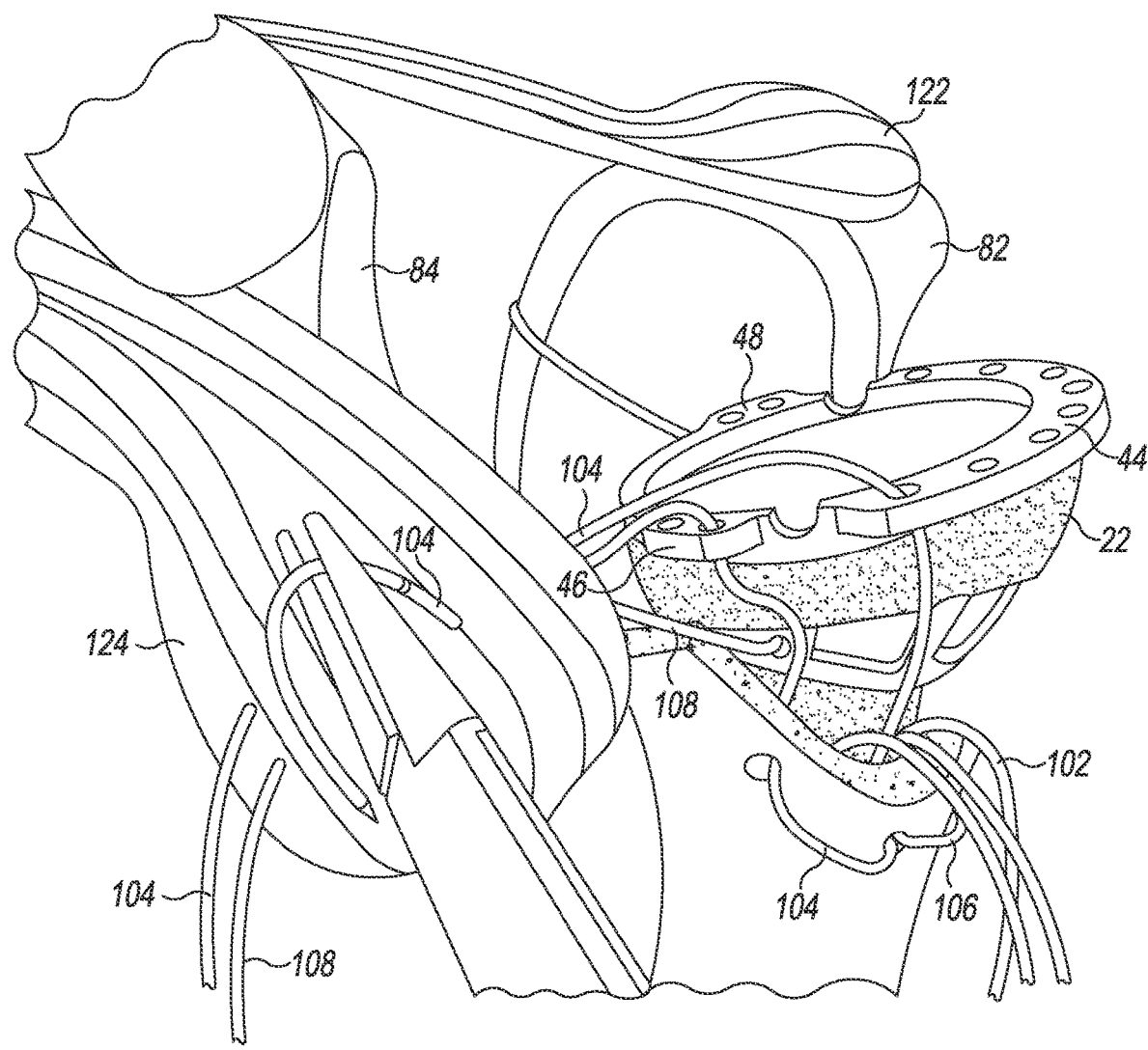

As shown in FIGS. 11 and 12, the surgeon then advances the posterior limb of the "around-the-world" suture 108 through the greater tuberosity rotator tendon 122 near the bone/tendon interface. The process is repeated with the anterior limb of suture 108 being passed through the lesser tuberosity rotator tendon 124.

Figure 13:
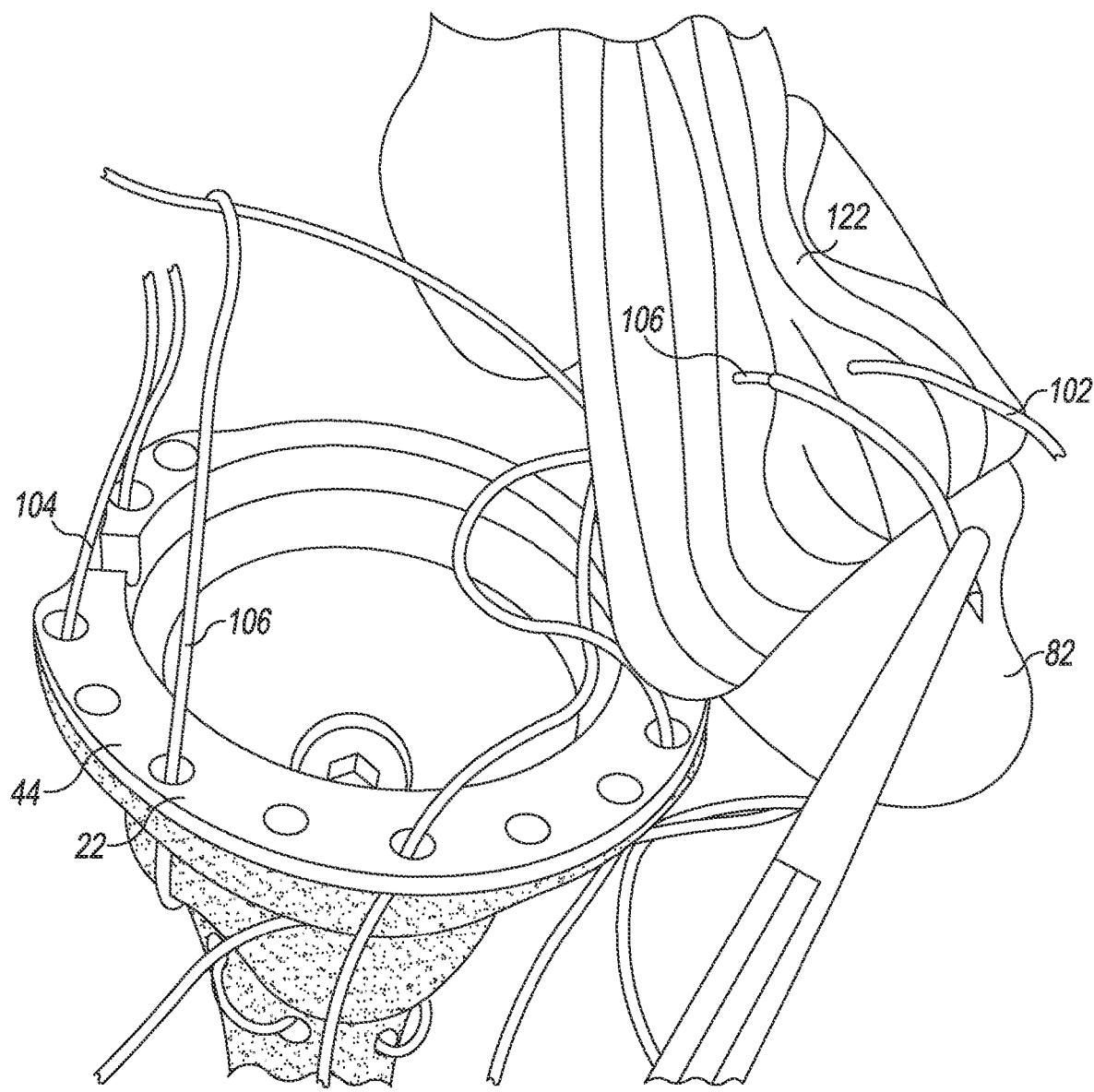

As shown in FIG. 12, one end of the suture 104 is advanced through one of the suture holes 50 on the anterior side of the lateral suture collar 44 with the other end of the suture 104 being advanced through one of the suture holes 50 of the anteromedial suture collar 46. Both ends of the suture 104 are then passed through the rotator tendon 124 near the tendon/lesser tuberosity interface. This process is repeated by passing one end of the suture 102 through one of the suture holes 50 on the posterior side of the lateral suture collar 44, the other end through a suture hole 50 on the posteromedial suture collar 48, and then passing both ends through the greater tuberosity rotator tendon 122 near the bone/tendon interface. Likewise, as shown in FIG. 13, the ends of the suture 106 are passed through separate suture holes 50 on the lateral side of the lateral suture collar 44. Thereafter, one end of the suture 106 is passed through the greater tuberosity rotator tendon 122 near the bone/tendon interface, with the other end of the suture 106 being passed through the lesser tuberosity rotator tendon 124 near the bone/tendon interface.

Figure 14:
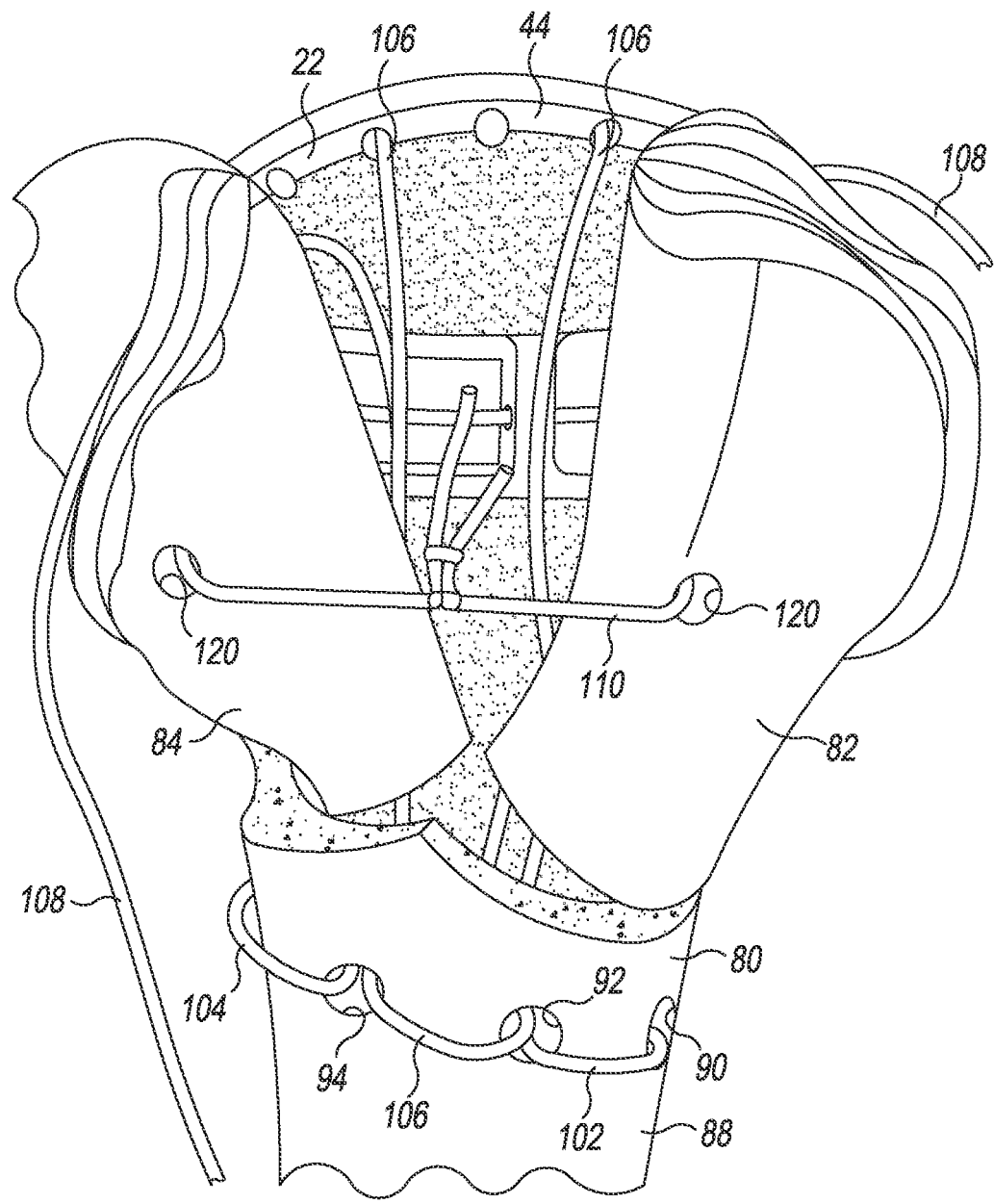

Referring now to FIG. 14, one end of the suture 110 (see also FIG. 10) is passed through the drilled hole 120 in the greater tuberosity 82, with the other end of the suture 110 being passed through the drilled hole 120 in the lessor tuberosity 84. The suture 110 is then tensioned and tied to bring the tuberosities 82, 84 together and secure them to the modular reverse shoulder orthopaedic implant 10.

Figure 15:
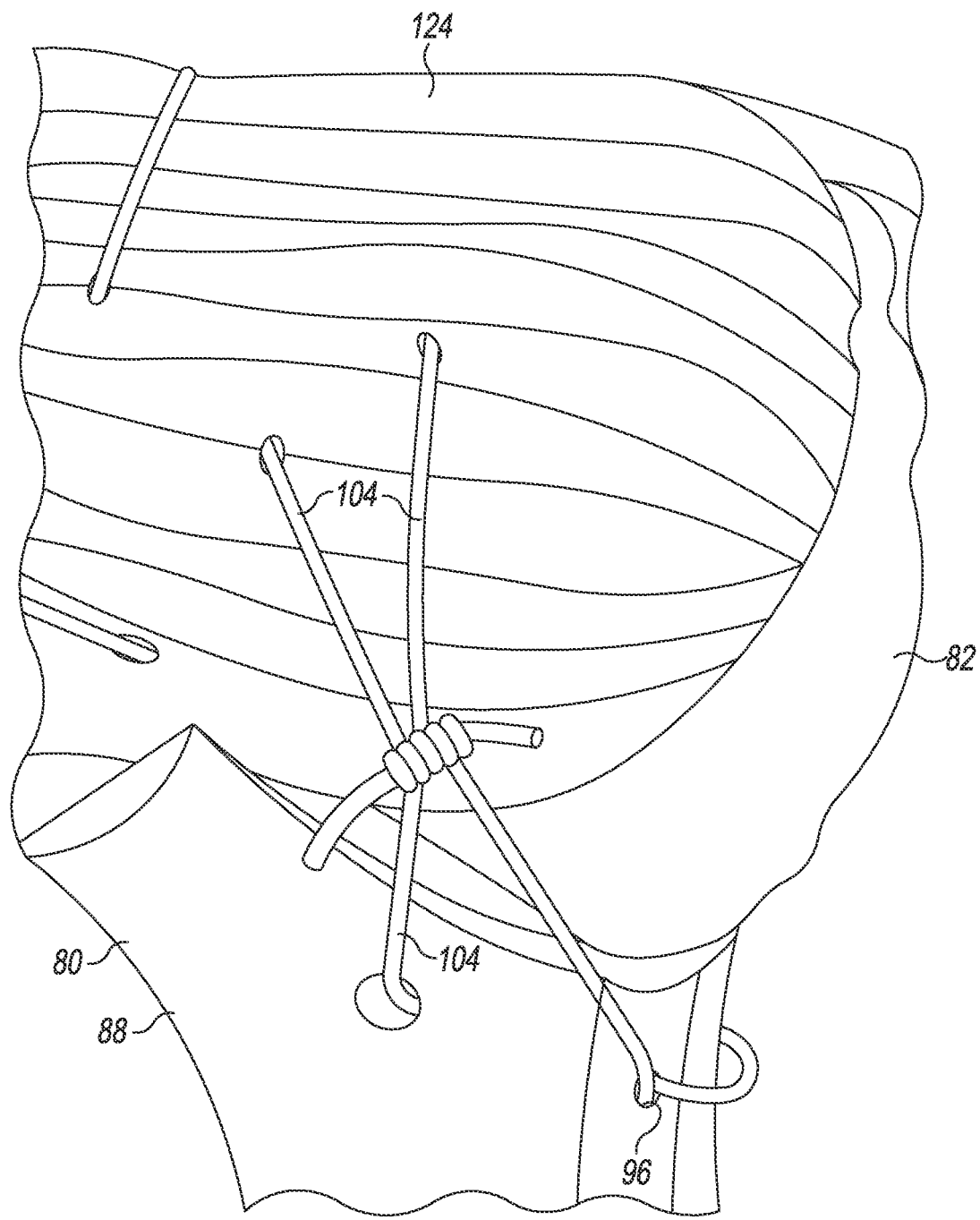

As shown in FIG. 15, the surgeon then advances the end of suture 104 that passes through the drilled bone hole 96, the anteromedial suture collar 46, and the lessor tuberosity rotator tendon 124 back down and under the loop created between the drilled bone hole 94 and the drilled bone hole 96. The suture 104 is then tensioned upwardly thereby pulling the loop up onto the lesser tuberosity 84 and creating a modified "FIG. 8". The surgeon then ties and trims the excess suture 104.

Figure 16:
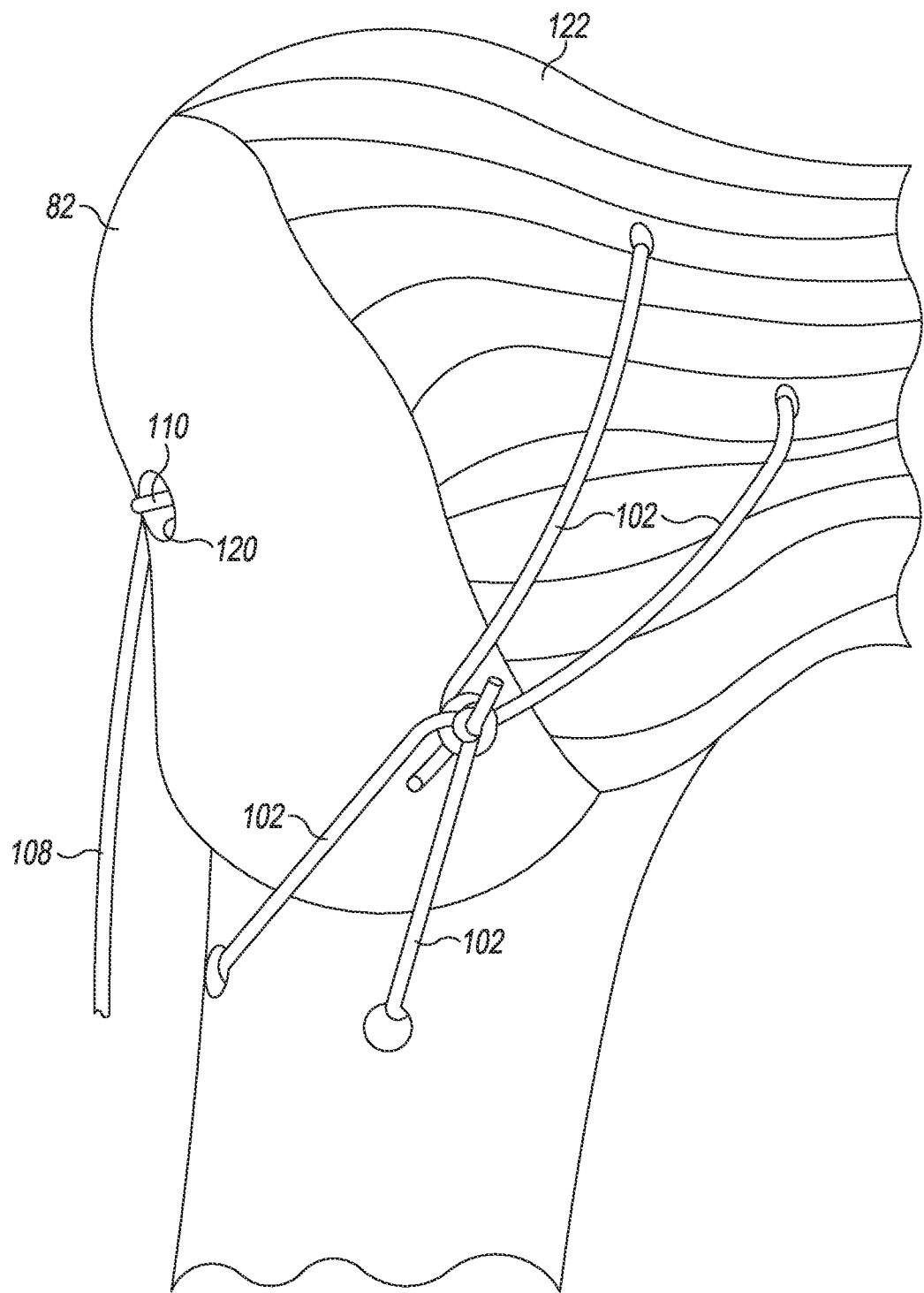

The surgeon repeats the process, as shown in FIG. 16, by advancing the end of suture 102 that passes through the drilled bone hole 90, the posteromedial suture collar 48, and the greater tuberosity rotator tendon 122 back down and under the loop created between the drilled bone hole 90 and the drilled bone hole 92. The suture 102 is then tensioned upwardly thereby pulling the loop up onto the greater tuberosity 82 and creating a modified "FIG. 8". The surgeon then ties and trims the excess suture 102.

Figure 17:
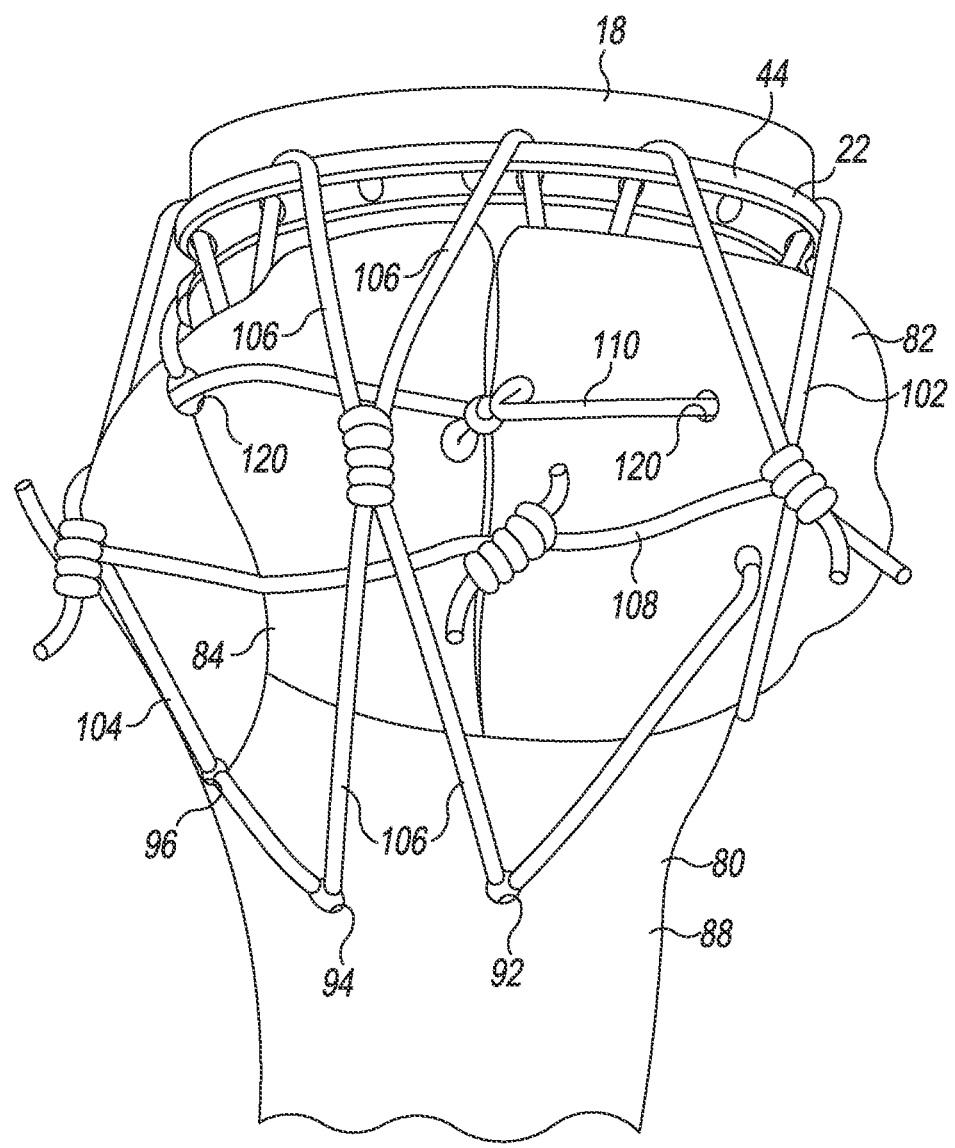
Figure 18:
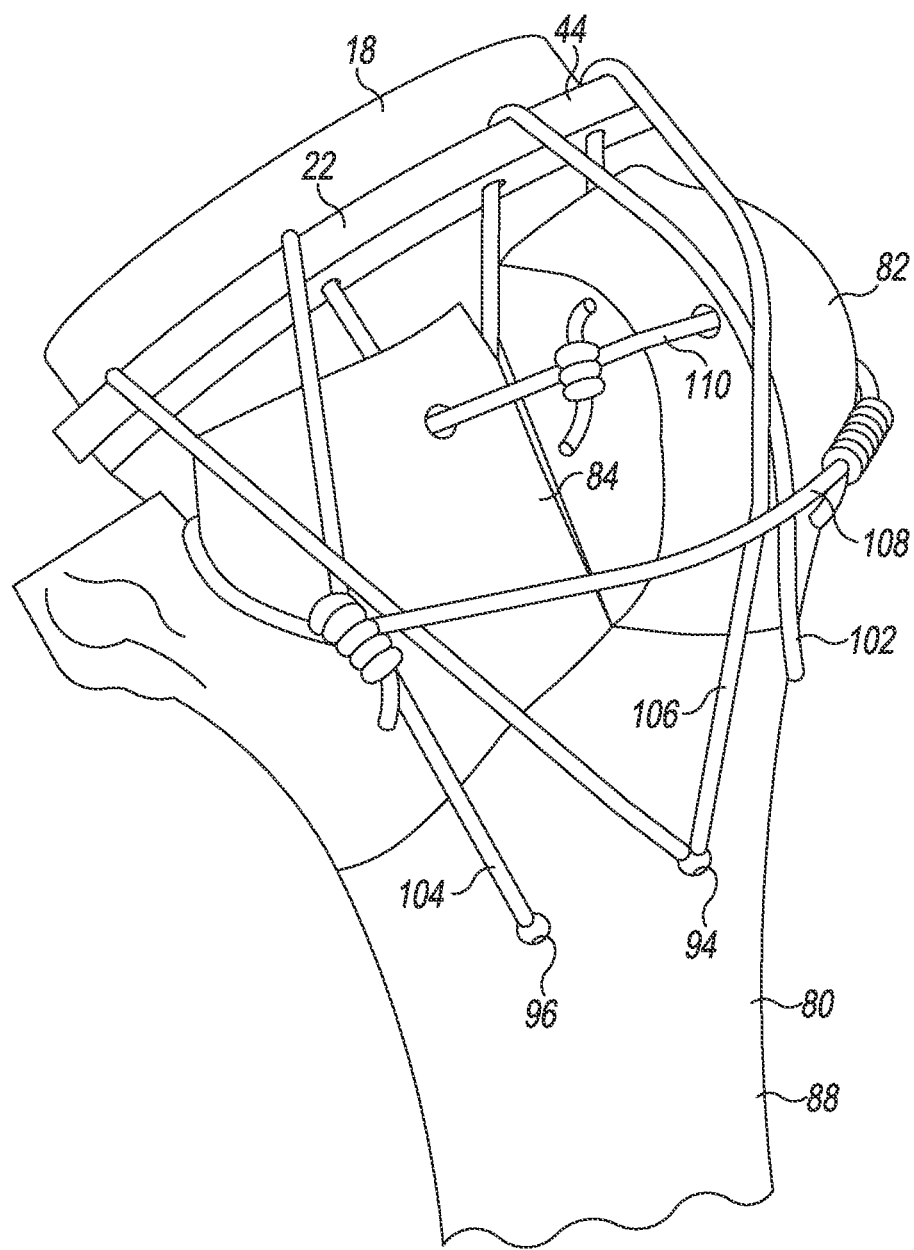

As shown in FIGS. 17 and 18, the surgeon then passes the end of suture 106 from drilled bone hole 92 down under the loop created between drilled bone hole 92 and drilled bone hole 94. The surgeon then tensions the suture 106 upwards thereby pulling the loop up onto the greater tuberosity 82 and creating a modified "FIG. 8". The surgeon then ties and trims the excess suture 106. Both ends of the "around-the-world" suture 108 are then tensioned, tied together around both tuberosities 82, 84, and trimmed to provide additional stability to the fracture reduction.

The surgeon then completes the remaining surgical steps, such as installation of the humeral cup 18 and installation of the glenosphere component 12. The surgeon then closes the surgical site.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. A modular reverse shoulder orthopaedic implant, comprising:
   an elongated humeral stem component configured to be implanted into a humerus of a patient,
   a fracture epiphysis component separable from the humeral stem component, the fracture epiphysis component comprising (i) a cup-shaped body having an annular rim formed in a superior end thereof, (ii) a lateral suture collar extending outwardly from the annular rim of the cup-shaped body within a segment of the annular rim defined by an anterior-most point of the rim and a posterior-most point of the rim, the lateral suture collar having a plurality of suture holes formed in a superior surface thereof, (iii) an anteromedial suture collar extending outwardly from the annular rim of the cup-shaped body within a segment of the annular rim defined by the anterior-most point of the rim and a medial-most point of the rim, the anteromedial suture collar having a plurality of suture holes formed in a superior surface thereof, and (iv) an posteromedial suture collar extending outwardly from the annular rim within a segment of the annular rim defined by the posterior-most point of the rim and the medial-most point of the rim, the posteromedial suture collar having a plurality of suture holes formed in a superior surface thereof, wherein (a) the lateral suture collar is discontiguous with the anteromedial suture collar and the posteromedial suture collar, and (b) the anteromedial suture collar and the posteromedial suture collar are discontiguous with one another,
   a locking screw secured to the humeral stem component and the fracture epiphysis component, and
   a humeral cup component secured to the fracture epiphysis component, the humeral cup component having a concave bearing surface configured to articulate with a rounded head surface of a glenosphere component
   wherein (i) an outer surface of the cup-shaped body of the fracture epiphysis component has a plurality of suture pockets formed in an inferior end thereof, (ii) each of the plurality of suture pockets formed in the cup-shaped body of the fracture epiphysis component is separated by a wall, and (iii) each of the walls separating the plurality of suture pockets formed in the cup-shaped body of the fracture epiphysis component has a suture hole formed therein.

2. The modular reverse shoulder orthopaedic implant of claim 1, wherein:
   the plurality of suture holes of each of the lateral suture collar, the anteromedial suture collar, and the posteromedial suture collar are positioned radially on each of the lateral suture collar, the anteromedial suture collar, and the posteromedial suture collar, respectively.

3. The modular reverse shoulder orthopaedic implant of claim 1, wherein the lateral suture collar is longer than both the anteromedial suture collar and the posteromedial suture collar.

4. The modular reverse shoulder orthopaedic implant of claim 1, wherein the anteromedial suture collar and the posteromedial suture collar are similar in size and face opposite one another along the annular rim of the cup-shaped body.

5. The modular reverse shoulder orthopaedic implant of claim 1, wherein:
   the outer surface of the cup-shaped body of the fracture epiphysis component has an additional suture hole extending therethrough, and
   the additional suture hole extends in the anteroposterior direction.

6. The modular reverse shoulder orthopaedic implant of claim 1, wherein:
   the outer surface of the cup-shaped body of the fracture epiphysis component has a number of additional suture holes extending therethrough, and
   each of the additional suture holes extends in the anteroposterior direction.

7. The modular reverse shoulder orthopaedic implant of claim 1, wherein the lateral suture collar, the anteromedial suture collar, and the posteromedial suture collar are coplanar.

* * * * *